(12) United States Patent
Khabashesku et al.

(10) Patent No.: US 7,919,640 B2
(45) Date of Patent: Apr. 5, 2011

(54) SYNTHESIS WITH METAL METHACRYLATES AS COMONOMERS

(75) Inventors: Olga Khabashesku, Houston, TX (US); Scott Cooper, Humble, TX (US)

(73) Assignee: Fina Technology, Inc., Houston, TX (US)

( * ) Notice: Subject to any disclaimer, the term of this patent is extended or adjusted under 35 U.S.C. 154(b) by 88 days.

(21) Appl. No.: 12/346,739

(22) Filed: Dec. 30, 2008

(65) Prior Publication Data

US 2010/0168345 A1 Jul. 1, 2010

(51) Int. Cl.
*C07F 7/00* (2006.01)
*C08G 18/62* (2006.01)

(52) U.S. Cl. .......................... 556/55; 525/451

(58) Field of Classification Search .................... 556/55; 525/451
See application file for complete search history.

(56) References Cited

U.S. PATENT DOCUMENTS

| | | |
|---|---|---|
| 3,966,902 A | 6/1976 | Chromecek |
| 4,278,735 A | 7/1981 | Marcantonio et al. |
| 4,500,466 A | 2/1985 | Hayes et al. |
| 4,730,067 A | 3/1988 | Filachek et al. |
| 4,766,174 A | 8/1988 | Statz |
| 4,895,827 A | 1/1990 | Vervacke et al. |
| 4,933,405 A | 6/1990 | Evani |
| 5,120,794 A | 6/1992 | Oberster et al. |
| 5,202,363 A | 4/1993 | Oberster et al. |
| 5,540,813 A | 7/1996 | Sosa et al. |
| 5,597,879 A | 1/1997 | Ase et al. |
| 5,616,681 A | 4/1997 | Itoh et al. |
| 5,721,009 A | 2/1998 | Dougherty et al. |
| 5,756,586 A | 5/1998 | Nishimura et al. |
| 5,844,039 A | 12/1998 | Scranton et al. |
| 6,194,504 B1 | 2/2001 | Nagel et al. |
| 7,179,873 B2 | 2/2007 | Reimers et al. |
| 2003/0073792 A1 | 4/2003 | Moore |
| 2004/0048987 A1 | 3/2004 | Campbell et al. |
| 2006/0167149 A1 | 7/2006 | Reimers et al. |
| 2008/0051540 A1 | 2/2008 | Reimers et al. |

OTHER PUBLICATIONS

Kickelbick et al., J.Chem.Soc., Dalton Trans. vol. 20, pp. 3892-3898 (2002).*
Eisenberg et al., Macromolecules, vol. 23, No. 18, pp. 4098-4107 (1990).*
Eisenberg, A., Kim, J.S., "Introduction to Ionomers", Wiley Interscience, 1998< New York, NY.*
Gotoh, Y. et al., "Preparation and Viscoelastic Behavior of Methacrylate Ionomers Crosslinked by Titanium (IV), Zirconium (IV), and Nb (V) Ions", Polymer Journal, vol. 36, No. 3, pp. 255-260 (2000).*
Veyland, A. et al., "Aqueous Chemistry of Zirconium (VI) in Carbonate Media", Helvetica Chimica Acta, vol. 83, pp. 414-427 (2000).*

(Continued)

*Primary Examiner* — Porfirio Nazario Gonzalez
(74) *Attorney, Agent, or Firm* — Bradley A. Misley

(57) ABSTRACT

A method for the in-situ preparation of an ionic comonomer from its chemical precursors, prepared in a solution of styrene monomer is disclosed. In one embodiment, the ionic comonomer is zirconium methacrylate, $Zr(MA)_4$ or zirconyl methacrylate, $ZrO(MA)_2$, or a combination thereof, and zirconium carbonate hydroxide oxide, $ZrCO_3(OH)_2 \cdot ZrO2$, and methacrylic acid, $CH_2=C(CH_3)-COOH$, are used as precursors used for its in-situ preparation.

15 Claims, 1 Drawing Sheet

Coordination complex of Zr(IV) and methacrylic acid

OTHER PUBLICATIONS

Yuan X. et al., "In-situ Preparation of Zinc Unsaturated Carboxylic Acids Salts to Reiforce NBR", Journal of Applied Polymer Science, vol. 77, Issue 12, pp. 2740-2748 (2000).*

Yuan X. et al., "In-situ Preparation of Magnesium methacrylate to Reiforce NBR", Journal of Applied Polymer Science, vol. 84, Issue 7, pp. 1403-1408 (2002).*

I. Capek, "Nature and Properties of Ionomers Assemblies", Advances in Colloid and Interface Science, vol. 118, pp. 73-112 (2005).*

Dennes et al., Journal of the American Chemical Society, vol. 129, No. 1, pp. 93-97 (2007).*

U.S. Appl. No. 12/346,729, filed Dec. 30, 2008, Khabashesku et al.

U.S. Appl. No. 12/346,743, filed Dec. 30, 2008, Khabashesku et al.

* cited by examiner

Coordination complex of Zr(IV) and methacrylic acid

SYNTHESIS WITH METAL METHACRYLATES AS COMONOMERS

CROSS-REFERENCE TO RELATED APPLICATIONS

Not applicable

FIELD

The present invention generally relates to the production of polymer compounds and more particularly to the production of polystyrene.

BACKGROUND

General purpose polystyrene (GPPS) is made from styrene, a vinyl aromatic monomer that can be produced from aromatic hydrocarbons, for example those derived from petroleum. GPPS is useful in a variety of applications, such as casing for appliances, molded into toys or utensils, or expanded to create foamed styrene. In most cases, GPPS is a hard and brittle plastic, however, the use of comonomers may alter its physical properties, for example, styrene can be copolymerized with polybutadiene to make SBS polymer. The resulting SBS polymer has more rubber-like qualities, such as elastomeric performance and abrasion resistance. Other polymers can also experience altered physical properties when polymerized using comonomers. Ionic comonomers, for example, may alter the properties of a polymer, such as melt flow rate, melt strength, polydispersity, and glass transition temperature.

When ionic comonomers are used, the polymer product can be referred to as an ionomer. An ionomer is a polymer that contains nonionic repeating units and a small portion of ionic repeating units. Generally, the ionic groups make up less than 15% of the polymer. The ionic groups are attached to the polymer backbone at random intervals and can reversibly associate with one another, creating reversible crosslinks. These reversible crosslinks can cause the product polystyrene to be less brittle and more resistant to abrasions. Ionic aggregates in the copolymer can also affect such properties as bending modulus, tensile strength, impact resistance, melt strength, glass transition temperature and melt viscosity.

Unsaturated carboxylic acid salts are a group of ionic comonomers that can serve as effective crosslinking agents. Metal methacrylates are an example of carboxylic acid salts. One metal methacrylate that may be useful as an ionomeric crosslinker is zinc dimethacrylate, $Zn(MA)_2$. It is a divalent metal and therefore, capable of forming two reversible crosslinks with the ionized acid ends of the methacrylates that are incorporated into the backbones of polystyrene chains. Zinc has the disadvantage of being listed on the EPA list of hazardous metals, requiring specialized procedures and monitoring due to the environmental hazard it presents.

Other metal methacrylates that may be useful as an ionomeric crosslinker are zirconium based compounds, such as zirconium methacrylate, $Zr(MA)_4$, or zirconyl dimethacrylate, $ZrO(MA)_2$. Zirconium is a fairly abundant element, is not listed on the EPA list of hazardous metals, and some zirconium precursors are commercially available at costs lower than that of zinc containing precursors. These precursors may be in powder form, which can provide difficulty in measuring and handling of the materials, and are insoluble in styrene.

In view of the above, it would be desirable to have a method for the in-situ preparation of zirconium methacrylate compounds from relatively inexpensive precursors that can be used in conjunction with styrene polymerization.

SUMMARY

Embodiments of the present invention generally include a method for the in-situ preparation of an ionic comonomer from its chemical precursors, formed in a solution of styrene monomer. The method involves adding chemical precursors to a reaction vessel containing styrene monomer, allowing the comonomer to form and dissolve in the styrene monomer either by stirring or exposing to elevated temperatures or both, removing unwanted side products, and diluting the solution with styrene until a mixture useful for styrene polymerization is obtained.

In one embodiment, the ionic comonomer is either zirconium methacrylate, $Zr(MA)_4$, or zirconyl methacrylate, $ZrO(MA)_2$, or a combination thereof. According to the same embodiment, the chemical precursors used are zirconium carbonate hydroxide oxide, $ZrCO_3(OH)_2.ZrO2$, and methacrylic acid, $CH_2=C(CH_3)-COOH$. The precursors can be added to the styrene monomer in a zirconium to methacrylic acid molar ratio from 1:2 to 1:6. A molar ratio of 1:2 generally results in the formation of zirconyl methacrylate. A molar ratio of 1:4 generally results in the formation of zirconium methacrylate. A molar ratio of 1:6 generally results in zirconium methacrylate plus two additional molar equivalents of methacrylic acid. Because zirconium has a coordination number of six that is greater than its oxidation number of four, it is able to form coordination complexes with the additional methacrylic acid.

Another embodiment of the present invention is a method for the in-situ preparation of an ionic comonomer in styrene monomer by contacting chemical precursors of an ionic comonomer in a reaction vessel containing styrene monomer and producing a first product comprising the ionic comonomer in solution with the styrene monomer. The formation of the first product can be assisted via stirring, elevated temperature, or a combination thereof. The method can include removing unwanted side products from the first product and can include diluting the first product by adding additional styrene monomer. The ionic comonomer can be zirconium methacrylate, $Zr(MA)_4$, or zirconyl methacrylate, $ZrO(MA)_2$, or a combination thereof. The chemical precursors of the ionic comonomer can be zirconium carbonate hydroxide oxide, $ZrCO_3(OH)_2.ZrO2$, and methacrylic acid, $CH_2=C(CH_3)-COOH$, which can be added in a molar ratio of zirconium to methacrylic acid from 1:1 to 1:20. Water produced as an unwanted side product can be removed from the first product, such as by draining and/or by passing the reaction mixture through a dehydration process. The water produced as an unwanted side product can also be removed from the first product by passing the reaction mixture over an alumina bed. An embodiment of the invention can be a polymer containing an ionic comonomer produced according to the method, such as a polystyrene polymerized with an in-situ formed ionic comonomer and can be an article made from a the polystyrene.

Yet another embodiment of the present invention is a method for the in-situ preparation of an ionic comonomer in styrene monomer by contacting zirconium carbonate hydroxide oxide, $ZrCO_3(OH)_2.ZrO2$, and methacrylic acid, $CH_2=C(CH_3)-COOH$, in a molar ratio of zirconium to methacrylic acid from 1:1 to 1:10, in a reaction vessel containing styrene monomer and producing a first product comprising either zirconium methacrylate, $Zr(MA)_4$, or zirconyl methacrylate, $ZrO(MA)_2$, or a combination thereof, in solution with the styrene monomer. An embodiment can further be a polymer containing an ionic comonomer produced according to the above method or an article made from a polymer made according to the method.

DETAILED DESCRIPTION

Figure 1:
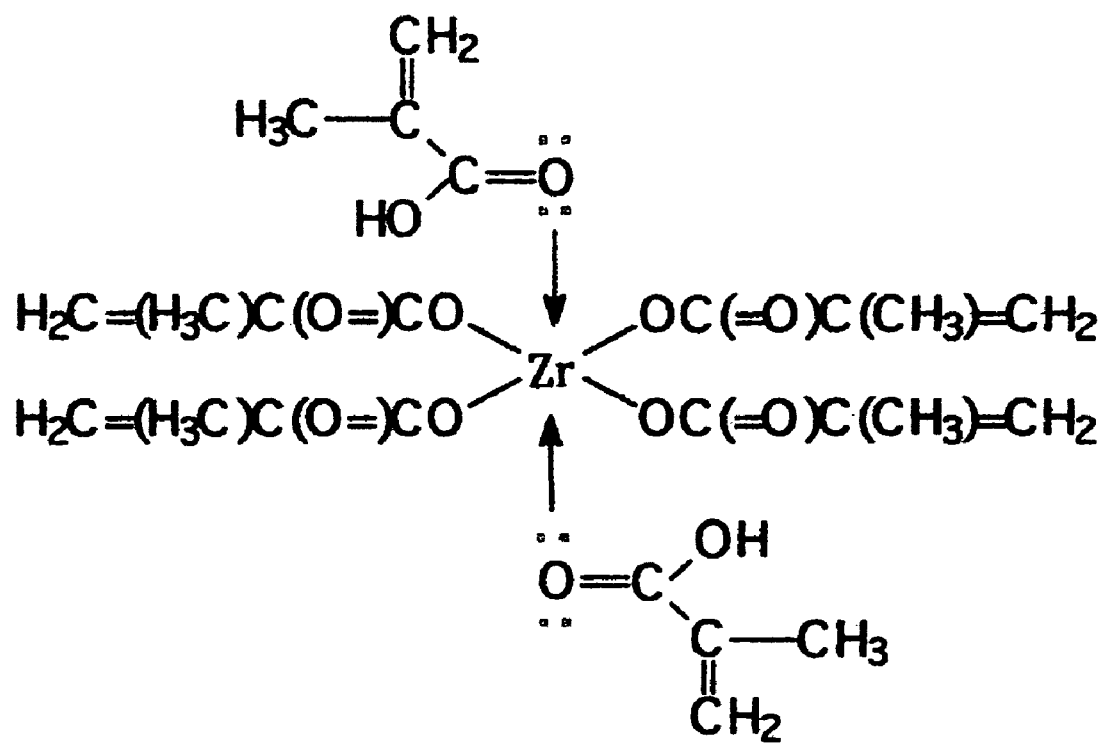
FIG. 1 illustrates a coordination complex comprising Zr(IV) and methacrylic acid.

GPPS can be made using many ionic comonomers. These ionic comonomers generally comprise an unsaturated moiety, an anionic moiety, and a cationic moiety. Unsaturated carboxylic acid salts, for example, can be used. Metal methacrylates, such as zinc methacrylate and zirconium methacrylate, are in this group. Zirconium based methacrylates, for a variety of reasons, may be less expensive and more efficient than others as an ionic comonomer in GPPS production.

Zirconium is a widely available element and both zirconium methacrylate and zirconyl methacrylate, are more soluble in styrene than is zinc methacrylate. Also, many metals, such as zinc, are listed on the EPA's list of hazardous metals, requiring special procedures to limit the metal's presence in wastewater. The monitoring of wastewater can result in increased expenses. Zirconium, on the other hand, is not EPA listed, and therefore, poses less of an environmental hazard and eliminates the extra cost of wastewater monitoring.

Zirconium may also function as a more efficient crosslinker than zinc because it is tetravalent. Tetravalent metals have the advantage of being able to bond with up to four of the ionized acidic ends of methacrylates incorporated into the backbones of polystyrene chains. The unsaturated double bond of methacrylate allows incorporation, via free-radical polymerization, into the polystyrene chain. Thus, when a metal makes bonds to more than one carboxylic acid, it can form reversible crosslinks between chains, which can alter the thermoplastic properties of the product, such as melt strength, polydispersity, and glass transition temperature. Zirconium has a coordination number of six that is greater than its oxidation number of four. Thus, the metal tends to use its vacant d-orbital to accept oxygen lone pairs from other acid residues of the copolymer chains and form charge transfer complexes.

FIG. 1 shows an example of a charge transfer complex with a zirconium metal center. The metal center has ionic bonds with the ionized acidic ends of four methacrylates. Two additional methacrylic acids coordinate with the metal center by donating oxygen lone pairs to the vacant d-orbital of the metal and forming a charge transfer complex. A charge transfer complex is defined as an electron donor-electron acceptor complex, characterized by electronic transition to an excited state. This excited state produces an observable color change. Almost all charge transfer complexes have unique and intense absorption bands in the ultraviolet-visible region. Thus, the formation of coordination complexes with Zr can be confirmed with UV-V is spectra.

The present invention includes a method for the in-situ synthesis of a zirconium containing methacrylate complex that can be a comonomer used in styrene polymerizations. The method involves the addition of zirconium carbonate hydroxide oxide and methacrylic acid to a solution of styrene monomer to form a solution comprising zirconium containing methacrylate complexes. The methacrylate products of the reaction of zirconium carbonate hydroxide oxide and methacrylic acid are soluble in styrene monomer. Zirconium carbonate hydroxide oxide $ZrCO_3(OH)_2 \cdot ZrO2$ is a commercially available precursor for styrene-soluble zirconium based crosslinkers. Inorganic zirconium carbonate hydroxide oxide is insoluble in styrene, but upon addition of methacrylic acid to the styrene containing the zirconium carbonate hydroxide oxide, can produce clear solutions. Thus, zirconium methacrylate and zirconyl methacrylate can be formed in-situ from readily available precursors.

The molar ratio of zirconium to methacrylic acid can be varied, for example from 1:1 to 1:20. Alternately molar ratio of zirconium to methacrylic acid in the chemical precursors can range from 1:1 to 1:10 or from 1:2 to 1:6.

EXAMPLES

Zirconium carbonate hydroxide oxide, $ZrCO_3(OH)_2 \cdot ZrO_2$, was placed in a laboratory scale vessel and styrene monomer was added. A white amorphous powder of zirconium carbonate hydroxide oxide did not dissolve in the styrene monomer, and the styrene layer remained clear above the inorganic starting material. Methacrylic acid, $CH_2=C(CH_3)-COOH$, was added to the vessel, and the reaction mixture became milky white with bubbles rising to the surface from the bottom layer of inorganic material. The reaction mixture was left overnight with stirring in a kettle at room temperature (22° C.-25° C.) in Preparation #1; at 40° C. in an oil bath in Preparation #2; and without stirring in a nitrogen purged oven at 40° C. loosely covered with a lid in Preparations #3, 4 and 5.

In Preparations #1, 3, 4 and 5, the white starting material zirconium carbonate hydroxide oxide completely dissolved in four to 14 hours and the reaction mixture formed two layers, a top layer of either clear or hazy styrene solution and a bottom layer with a minor volume of clear water. Preparation #2 was discarded because poor regulation of the oil bath temperature caused overheating of the reaction mixture up to 50° C., which led to gelling due to styrene polymerization. Amounts of the reagents, reaction conditions and descriptions of the product mixtures are shown in Table 1.

TABLE 1

Reagent amounts and reaction conditions for the preparations of zirconium methacrylates in styrene monomer.

| Prep # | Zirconium carb g | Styrene g | Meth. acid g | Temperature C | Stirring | Molar ratio Zr/MA | Product in org. layer |
|---|---|---|---|---|---|---|---|
| 1 | 31.08 | 197.72 | 69.32 | 25 | yes | 1:4 | hazy |
| 2 | 31.08 | 200.52 | 34.66 | 25 | yes | 1:2 | gel |
| 3 | 31.08 | 100.00 | 69.32 | 40 | no | 1:4 | clear |
| 4 | 31.08 | 125.00 | 103.98 | 40 | no | 1:6 | clear |
| 5 | 15.53 | 50.40 | 17.45 | 40 | no | 1:2 | clear |

As can be seen from Table 1, the reactions succeeded in forming an organic layer of zirconium methacrylate dissolved in styrene monomer. The reaction proceeded even without the use of stirring, as was the case for Preparations #3, 4, and 5. When the reaction was performed at a temperature of around 40° C. the reaction mixture did not require stirring. Also, as seen in the table, the molar ratio of Zr to MAA was varied, from 1:2 to 1:6. This is because zirconium carbonate hydroxide oxide can possibly form two different methacrylate products of zirconium (IV); either zirconyl dimethacrylate ZrO(MA)$_2$ or zirconium methacrylate Zr(MA)$_4$, or a mixture of both. Zirconyl dimethacrylate and zirconium methacrylate are commercially available compounds that are readily soluble in styrene at ambient temperature. Both may be used as efficient crosslinkers in styrene.

If zirconium carbonate hydroxide oxide and methacrylic acid are combined with a zirconium to methacrylic acid molar ratio of 1:4, then the product will be predominately zirconium methacrylate, as shown in Equation 1.

Equation 1. Formation of zirconium (IV) methacrylate

If zirconium carbonate hydroxide oxide and methacrylic acid are combined with a zirconium to methacrylic acid molar ratio of 1:2, then the product will be predominately zirconyl methacrylate, as shown in Equation 2.

Equation 2. Formation of zirconyl (IV) methacrylate

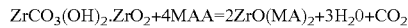

The water produced from the above reactions should not become a problem within the process if the loading of the zirconium methacrylate or zirconyl methacrylate is less than 2000 ppm by weight in the styrene monomer.

If the molar ratio of zirconium to methacrylic acid higher than 1:4 is employed, then predominately zirconium methacrylate will form and can be able to coordinate with additional molar equivalents of methacrylic acid due to the coordination number being higher than the valence number.

If a higher molar ratio of zirconium to methacrylic acid of 1:6 is employed, then predominately zirconium methacrylate will form and be able to coordinate with the two additional molar equivalents of methacrylic acid. Such coordination can be confirmed with UV-V is spectra.

The other products of Equations 1 and 2 also have implications for the procedure. The production of water can be a problem for polystyrene production, since only ~0.1% is generally tolerated in a typical styrene polymerization process. The layer of water which can form at the bottom of the reaction vessel must be drained. One method that may be useful for removing water is by passing the zirconium methacrylate solution in styrene through a dehydration process to remove the water content, such as by passing the zirconium methacrylate solution in styrene through an alumina bed.

The other side product of the reaction between zirconium carbonate hydroxide oxide and methacrylic acid is $CO_2$. Since carbon dioxide evolves in this reaction due to decomposition of displaced unstable carboxylic acid $H_2CO_3$, an elevated reaction temperature may be beneficial for zirconium carbonate thermal decomposition and may shift the reaction equilibrium to the right, removing $CO_2$ gas from the reaction zone. As one can see from the reaction conditions in Table 1, 40° C. appears to supply sufficient heating to aid reaction of MAA with zirconium carbonate without causing polymerization of the styrene. Accidental heating to 50° C. in the case of Preparation #2 turned out to be excessive, especially when accompanied with stirring, and promoted styrene polymerization.

Formation of soluble zirconium methacrylate in styrene has been completed in 3-15 hours, depending on the batch size. Depending on the amounts and concentrations of the reagents, dilution amount and reaction conditions, the formation of soluble zirconium methacrylate in styrene can take from 15 minutes to 30 hours.

The styrene solution of zirconium methacrylate can then be used as styrene comonomer in any known polymerization process for the production of polystyrene, such as GPPS. The styrene solution of zirconium methacrylate can be further diluted with styrene monomer if required. As a liquid that is pumpable and pourable, the zirconium methacrylate complex in styrene solution can be readily measured and transferred, which can facilitate its commercial use in a polystyrene production facility.

Use of broader terms such as comprises, includes, having, etc. should be understood to provide support for narrower terms such as consisting of, consisting essentially of, comprised substantially of, etc.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. A method for the in-situ preparation of an ionic comonomer in styrene monomer comprising:
    contacting chemical precursors of an ionic comonomer in a reaction vessel containing styrene monomer; and
    producing a first product comprising the ionic comonomer in solution with the styrene monomer;
    wherein the chemical precursors of the ionic comonomer are zirconium carbonate hydroxide oxide, ZrCO3(OH)2.ZrO2, and methacrylic acid, CH2=C(CH3)—COOH.

2. The method of claim 1, further comprising:
    facilitating the formation of the first product via. stirring, elevated temperature, or a combination thereof 3. The method of claim 1, further comprising:
    removing unwanted side products from the first product.

4. The method of claim 1, further comprising:
    diluting the first product by adding additional styrene monomer.

5. The method of claim 1, wherein the ionic comonomer is either zirconium methacrylate, Zr(MA)4, or zirconyl methacrylate, ZrO(MA)2, or a combination thereof.

6. The method of claim 1, wherein the chemical precursors are added in a molar ratio of zirconium to methacrylic acid from 1:1 to 1:20.

7. The method of claim 1, wherein the chemical precursors are added in a molar ratio of zirconium to methacrylic acid from 1:2 to 1:6.

8. The method of claim 1, wherein water produced as an unwanted side product is removed from the first product.

9. The method of claim 8, wherein water produced as an unwanted side product is removed from the first product by passing the first product through a dehydration process.

10. The method of claim 8, wherein water produced as an unwanted side product is removed from the first product by passing the first product over an alumina bed.

11. A method for the in-situ preparation of an ionic comononier in styrene monomer comprising:

contacting zirconium carbonate hydroxide oxide, $ZrCO_3(OH)_2 \cdot ZrO_2$, and methacrylic acid, $CH_2=C(CH_3)-COOH$, in a molar ratio of zirconium to methacrylic acid from 1:1 to 1:10, in a reaction vessel containing styrene monomer; and producing a first product comprising either zirconium methacrylate, $Zr(MA)_4$, or zirconyl methacrylate, $ZrO(MA)_2$, or a combination thereof, in solution with the styrene monomer.

12. The method of claim 11, wherein water produced as an unwanted side product is removed from the first product.

13. The method of claim 11, further comprising:
facilitating the formation of the first product via stirring, elevated temperature. or a combination thereof.

14. The method of claim 11, further comprising:
diluting the first product by adding additional styrene monomer.

15. The method of claim 11, wherein the zirconium carbonate hydroxide oxide and methacrylic acid are added in a molar ratio of zirconium to methacrylic acid from 1:2 to 1:6.

* * * * *